(12) United States Patent
    Schaefer

(10) Patent No.: US 10,413,433 B2
(45) Date of Patent: Sep. 17, 2019

(54) SYSTEM FOR CONNECTING A MEDICAL IMPLANT TO AN INSERTION AID

(71) Applicant: PFM MEDICAL AG, Cologne (DE)

(72) Inventor: Joachim Schaefer, Nonnweiler (DE)

(73) Assignee: PFM MEDICAL AG, Cologne (DE)

( * ) Notice: Subject to any disclaimer, the term of this patent is extended or adjusted under 35 U.S.C. 154(b) by 566 days.

(21) Appl. No.: 15/100,004

(22) PCT Filed: Nov. 24, 2014

(86) PCT No.: PCT/EP2014/075389
§ 371 (c)(1),
(2) Date: May 27, 2016

(87) PCT Pub. No.: WO2015/078807
PCT Pub. Date: Jun. 4, 2015

(65) Prior Publication Data
US 2017/0000632 A1    Jan. 5, 2017

(30) Foreign Application Priority Data

Nov. 29, 2013   (DE) .................... 20 2013 105 452 U

(51) Int. Cl.
*A61B 17/12*       (2006.01)
*A61F 2/95*        (2013.01)
(Continued)

(52) U.S. Cl.
CPC .......... *A61F 2/95* (2013.01); *A61B 17/12022* (2013.01); *A61B 17/12109* (2013.01);
(Continued)

(58) Field of Classification Search
CPC ...... A61B 17/12022; A61B 2017/1205; A61B 2017/12054; A61B 2017/12905;
(Continued)

(56) References Cited

U.S. PATENT DOCUMENTS 5,101,213 A * 3/1992 Harada ................. H01Q 1/088
                                                343/715
5,234,437 A * 8/1993 Sepetka ........... A61B 17/12022
                                                600/585
(Continued)

FOREIGN PATENT DOCUMENTS

CN    101234034    8/2008
DE     10155191    5/2003
(Continued)

OTHER PUBLICATIONS

English translation of International Search Report from corresponding PCT application No. PCT/EP2014/075389 dated Mar. 2, 2015.
(Continued)

*Primary Examiner* — Darwin P Erezo
*Assistant Examiner* — Erin L Colello
(74) *Attorney, Agent, or Firm* — Grossman, Tucker, Perreault & Pfleger, PLLC

(57) ABSTRACT

The invention relates to a system for connecting a medical implant to an insertion aid, comprising: a first spiral connecting device at the proximal end of the medical implant, a second spiral connecting device at the distal end of the insertion aid, a core wire, which in a first operating state of the system fixes the first spiral connecting device and the second spiral connecting device in relation to one another, wherein in the first operating state the first spiral connecting device and the second spiral connecting device at least partially engage in one another and the core wire extends through the first spiral connecting device and the second spiral connecting device.

10 Claims, 2 Drawing Sheets

(51) Int. Cl.
*A61F 2/88* (2006.01)
*A61B 17/00* (2006.01)

(52) U.S. Cl.
CPC .......... *A61B 17/12145* (2013.01); *A61F 2/88* (2013.01); *A61B 2017/00867* (2013.01); *A61B 2017/12054* (2013.01); *A61F 2002/9511* (2013.01); *A61F 2210/0014* (2013.01)

(58) Field of Classification Search
CPC .......... A61B 17/1214; A61B 17/12109; A61B 2017/00867; A61B 17/12145; A61B 17/12172; A61B 2017/12095; A61F 2002/011; A61F 2230/0091; A61F 2/88; A61F 2/885; A61F 2/95; A61F 2210/0014; A61F 2002/9511; A61F 2/92; A61F 2002/9522; Y10T 403/459
See application file for complete search history.

(56) References Cited

U.S. PATENT DOCUMENTS

| | | | | |
|---|---|---|---|---|
| 5,250,071 | A * | 10/1993 | Palermo | A45D 42/24 128/898 |
| 5,282,478 | A * | 2/1994 | Fleischhaker, Jr. | A61M 25/0905 403/229 |
| 5,417,708 | A * | 5/1995 | Hall | A61B 17/12022 128/899 |
| 5,421,348 | A * | 6/1995 | Larnard | A61M 25/0905 600/434 |
| 5,578,074 | A * | 11/1996 | Mirigian | A61B 17/12022 606/108 |
| 5,725,534 | A * | 3/1998 | Rasmussen | A61B 17/12022 600/585 |
| 5,925,059 | A * | 7/1999 | Palermo | A61B 17/12022 606/191 |
| 6,526,979 | B1 * | 3/2003 | Nikolchev | A61B 17/12022 128/830 |
| 6,905,503 | B2 * | 6/2005 | Gifford, III | A61B 17/12022 606/108 |
| 8,257,422 | B2 * | 9/2012 | Schaeffer | A61M 25/01 623/1.11 |
| 2005/0079196 | A1 | 4/2005 | Henkes et al. | |
| 2006/0135986 | A1 * | 6/2006 | Wallace | A61B 17/12113 606/200 |
| 2006/0276834 | A1 * | 12/2006 | Balgobin | A61B 17/12022 606/200 |
| 2007/0270903 | A1 * | 11/2007 | Davis, III | A61B 17/12022 606/200 |
| 2008/0221654 | A1 * | 9/2008 | Buiser | A61B 17/12 623/1.11 |
| 2010/0125323 | A1 | 5/2010 | Berglund et al. | |
| 2011/0046610 | A1 * | 2/2011 | Schaeffer | A61M 25/01 604/533 |
| 2011/0295303 | A1 * | 12/2011 | Freudenthal | A61B 17/12022 606/200 |
| 2013/0245745 | A1 | 9/2013 | Vong et al. | |
| 2014/0058434 | A1 * | 2/2014 | Jones | A61B 17/1214 606/200 |

FOREIGN PATENT DOCUMENTS

| | | |
|---|---|---|
| DE | 102007038446 | 2/2009 |
| EP | 1728477 | 12/2006 |
| WO | 96/40024 | 12/1996 |
| WO | 2006/118863 | 11/2006 |
| WO | 2007/106495 | 9/2007 |

OTHER PUBLICATIONS

English translation of Written Opinion from corresponding PCT Appln. No. PCT/EP2014/075389, dated Jun. 4, 2015.

* cited by examiner

SYSTEM FOR CONNECTING A MEDICAL IMPLANT TO AN INSERTION AID

FIELD OF THE INVENTION

The invention relates to a system for connecting a medical implant to an insertion aid. An implant is an artificial device that is implanted into the human or animal body, which remains permanently or temporarily within the human or animal body.

An example for a medical implant is a so-called stent, which is inserted into a hollow organ of the human or animal body to keep it open. The stent can be for example a small wire frame of metal or synthetic fibre in a tubular form. Stents are used on the one hand in blood vessels, especially in the coronary vessels, to prevent a repeated occlusion after their expansion. On the other hand stents are used in the cancer treatment to keep stenosis open after their expansion that are caused by malignant tumors.

BACKGROUND

Furthermore medical implants are used in cardiac surgeries, wherein the medical implants are often used to occlude abnormal openings within the heart.

As far as possible such medical implants are implanted into the human or animal body using a minimal invasive method. During a minimal invasive method an access to a larger blood vessel within the human or animal body is created, via which a catheter is inserted into the human or animal body. Via the blood vessels the catheter is guided to the implantation site. Afterwards the medical implant is transported via the catheter using an insertion aid.

Usually medical implants consist of a memory-shaped material, such that the medical implant unfolds into a predefined shape after exiting the catheter. The medical implant is thus transported via the catheter to the implantation site using the insertion aid and unfolds into the predefined shape after exiting the catheter. After the medical implant has been correctly implanted at the implantation site in the human or animal body the connection between the insertion aid and the medical implant can be released.

Thus, the medical implant must be connected to the insertion aid as secure as possible during the transport via the catheter and at the same time be released easily from the insertion aid after implantation. From the prior art it is for example known to clamp the medical implant to a carrier wire of the insertion aid and to release the clamping connection after a successful implantation of the medical implant. Disadvantageous of such a connection between the medical implant and the insertion aid is that a relatively high force is necessary to release the connection between the implant and the carrier wire and furthermore the connection between the medical implant and the carrier wire, which bases on a friction force, can negatively be influenced for example by fluids, so that the connection between the medical implant and the carrier wire can be released too early.

SUMMARY

It is thus an object of the invention to provide a system for connecting a medical implant to an insertion aid, which provides during the implantation of the medical implant into the human or animal body a secure connection between the medical implant and the insertion aid and at the same time enables an easy release of the connection between the medical and the insertion aid after implantation of the medical implant. Furthermore the connection between the medical implant and the insertion aid should have a minimal diameter because of the usage during the minimal invasive surgery, preferably a diameter that is smaller or equal to the diameter of the medical implant respectively the insertion aid.

The object is solved according to the invention by a system for connecting a medical implant to an insertion aid comprising a first helical connecting member at the proximal end of the medical implant, a second helical connecting member at the distal end of the insertion aid, and a core wire, which in a first operating state of the system locks the first helical connecting member and the second helical connecting member relative to each other, wherein in the first operating state the first helical connecting member and the second helical connecting member at least partially engaged each other and the core wire extends through the first helical connecting member and the second helical connecting member.

The system according to the invention is thus designed that the turns of the first helical connecting member engage into the turns of the second helical connecting member and that the first helical connecting member and the second helical connecting member are fixed relative to each other using the core wire. Engaging in the sense of the invention is particularly a sideways sliding into each other of the helical connecting members. Consequently a secure connection between the insertion aid and the medical implant during the transport of the medical implant to the implantation site, for example via a catheter, is guaranteed. After successful implantation of the medical implant in the human or animal body the connection between the medical implant and the insertion aid can be released in that the core wire is retracted from the first helical connecting member of the medical implant and the second helical connecting member of the insertion aid so that the first and second helical connecting members are no longer fixed relative to each other.

The first operating state of the device according to the invention corresponds to the state during the transport of the medical implant to the implantation site, for example via a catheter. Thus, in the second operating state the connection between the medical implant and the insertion aid is released.

The proximal end of the medical device, for example of the medical implant, in the sense of the invention is the end of the medical device that is directed towards the user respectively the surgeon. The distal end of the medical device, for example of the insertion aid, in the sense of the invention is the end of the medical device that is located opposite to the user respectively the surgeon.

In a variant of the system according to the invention the insertion aid is a spiral, wherein the single turns of the spiral outside the first helical connecting member are preferably located directly adjacent to each other. The design of the insertion aid as a spiral has the advantage that the first helical connecting member can be created in an easy way in that the distance between the turns of the spiral in the area of the first helical connecting member is set to a predefined distance. In the area outside of the first helical connecting member the turns of the insertion aid are preferably located directly adjacent to each other so that the insertion aid is designed as a cylinder with a closed surface. Thus the insertion aid has a high stiffness in the longitudinal direction of the inlet guide and is at the same time flexible to follow for example a curved guide of the catheter through the vessels of the human or animal body.

According to a further variant of the system according to the invention the medical implant is designed as a spiral, wherein the single turns of the spiral outside the second helical connecting member are preferably at least partly located adjacent to each other. In the same way as an insertion aid designed as a spiral the second helical connecting member can be created in an easy way in that the single turns of the spiral of the medical implant are set to a predefined distance. In the implanted state the medical implant often has curves so that the medical implant designed as a spiral has turns in these areas that are at least in the inner area located adjacent to each other and at the same time they are slightly offset each other in the outer area.

In a particularly preferred variant of the system according to the invention the single turns of the first helical connecting member and/or the second helical connecting member are spaced from each other. In that way the first helical connecting member and the second helical connecting member can be nested into each other in an easy way and the core wire can be passed through the first and the second helical connecting member to fix the first operating state.

According to a particularly preferred variant of the system according to the invention the spacing of the single turns of the first helical connecting member and/or the second helical connecting member corresponds to 1.0 to 2.5 times the diameter of the wire of the first helical connecting member and/or the second helical connecting member. Thereby it is guaranteed that the first helical connecting member can be released from the second helical connecting member after the implantation of the medical implant and removal of the core wire.

According to a further variant of the system according to the invention the medical implant, the insertion aid, the first helical connecting member, the second helical connecting member and/or the core wire at least partly consist of a shape-memory material, preferably of a nickel-titanium alloy like nitinol.

Expediently the first helical connecting member or the second helical connecting member are built of a wire with a diameter between 0.3 mm and 1.5 mm, preferably between 0.5 mm and 1.0 mm and further preferred between 0.6 mm and 0.7 mm.

According to a preferred variant of the system according to the invention the first helical connecting member is arranged angled to the medical implant. Between the turns of the first helical connecting member and the medical implant a through hole is created by the angle between the first helical connecting member and the medical implant through which the core wire can pass. Thus, the core wire does not expand into the medical implant in the first operating state, which could have a negative influence on the unfolding of the medical implant during the implantation.

According to a variant of the invention the first helical connecting member or the second helical connecting member is curved along the longitudinal axis of the core wire, wherein the curved first helical connecting member or the second helical connecting member in the first operating state is fixed against elastic restoring forces in an elongated state along the longitudinal axis of the core wire by the core wire. After removing the core wire the first respectively second helical connecting member returns to the curved configuration due to elastic restoring forces, whereby the first helical connecting member withdraws from the second helical connecting member or vice versa. Thus, the connection between the first and the second helical connecting member automatically releases itself after removing the core wire.

According to an alternative variant of the system according to the invention the first helical connecting member and the second helical connecting member are curved along the longitudinal axis of the core wire, wherein the curvature of the first helical connecting member is opposite to the curvature of the second helical connecting member, and wherein the curved first and second helical connecting members in the first operating state are fixed against elastic restoring forces in an elongated state along the longitudinal axis of the core wire by the core wire. After removing the core wire the first helical connecting member and the second helical connecting member return to the curved configuration due to elastic restoring forces, so that the first helical connecting member removes from the second helical connecting member after removing the core wire.

According to a further variant of the system according to the invention the insertion aid is cylindrical and has a hollow space along the longitudinal axis, and wherein the core wire is located within the hollow space and movable relative to the insertion aid along the longitudinal axis of the insertion aid. Thus, the core wire is located movable within the hollow space of the insertion aid and is guided in the first operating state through the first helical connecting member of the medical implant and the second helical connecting member of the insertion aid, as soon as the first helical connecting member engages the second helical connecting member, so that the connection between the medical implant and the insertion aid is guaranteed in the first operating state.

According to a further variant of the invention the core wire has an enlarged cross section at the distal end, which is preferably larger than the inner diameter of the helical ends of the medical implant and the insertion aid. Thereby an accidentally release of the medical implant from the insertion aid is prevented. For example the core wire extends in the first operating state through the wall of the medical implant outwards and afterwards the substantially round cross section is deformed by crushing, also called imprinting, so that the cross section of the core wire is greater than the inner diameter of the helical end of the medical implant and the inlet guide. When releasing the medical implant the core wire is pulled with the enlarged cross section through the helical end of the medical implant and the insertion aid.

In the following the invention is described with respect to the embodiments shown in the figures.

DETAILED DESCRIPTION

Figure 1:
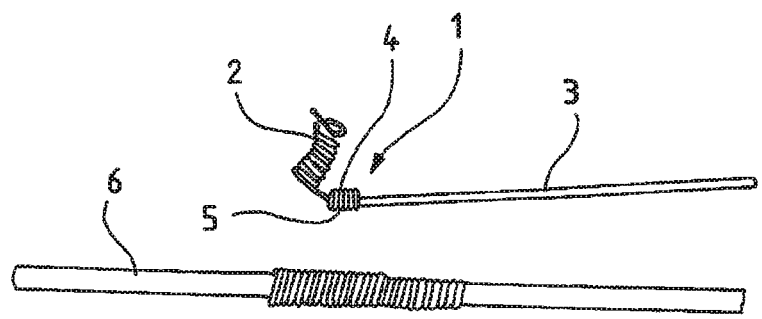
FIG. 1 is an inventive system for connecting a medical implant with an insertion aid in a first operating state.

In FIG. 1 is shown an inventive system 1 for connecting a medical implant 2 with an insertion aid 3 in a first operating state. The system 1 of FIG. 1 comprises a first helical connecting member 4 at the proximal end of the medical implant 2, a second helical connecting member 5 at the distal end of the insertion aid 3 and a core wire 6. In the first operating state of the inventive system 1 shown in FIG.

1 the first helical connecting member 4 of the medical implant 2 and the second helical connecting member 5 of the insertion aid 3 at least partially engage each other and the core wire 6 extends through the first and second helical connecting member 4, 5, so that the core wire 6 in the first operating state of the system 1 locks the first helical connecting member 4 and the second helical connecting member 5 relative to each other.

The insertion aid 3 of the system 1 according to the invention of FIG. 1 is a spiral, wherein the single turns of the spiral outside the first helical connecting member 4 are located directly adjacent to each other. The medical implant 2 of the system 1 according to the invention of FIG. 1 is also a spiral, wherein the single turns of the spiral outside the second helical connecting member 5 are at least partly located adjacent to each other.

As can be seen from FIG. 1 the single turns of the first helical connecting member 4 and the single turns of the second helical connecting member 5 are spaced from each other. The spacing of the single turns of the first helical connecting member 4 and the spacing of the single turns of the second helical connecting member 5 corresponds to 1.0 to 2.5 times the diameter of the wire of the first and second helical connecting members 4, 5, wherein the first helical connecting member 4 and/or the second helical connecting member 5 are built of a wire with a diameter between 0.3 mm and 1.5 mm, preferably between 0.5 mm and 1.0 mm and further preferred between 0.6 mm and 0.7 mm.

Expediently the medical implant 2, the insertion aid 3, the first helical connecting member 4, the second helical connecting member 5 and/or the core wire 6 at least partly consist of a shape-memory material, preferably of a nickel titanium alloy like nitinol. As can be further seen from FIG. 1 the first helical connecting member 4 is arranged angled to the medical implant 1. Thereby the core wire 6 can extend through the single turns of the first helical connecting member 4 outwardly, so that the core wire does not extend through the medical implant 2 and influenced his form. The insertion aid 3 of the system 1 according to the invention of FIG. 1 is cylindrical and has a hollow space along the longitudinal axis of the insertion aid 3. The core wire 6 of system 1 is located within the hollow space and is movable relative to the insertion aid 3 along the longitudinal axis of the insertion aid 3.

Figure 2:
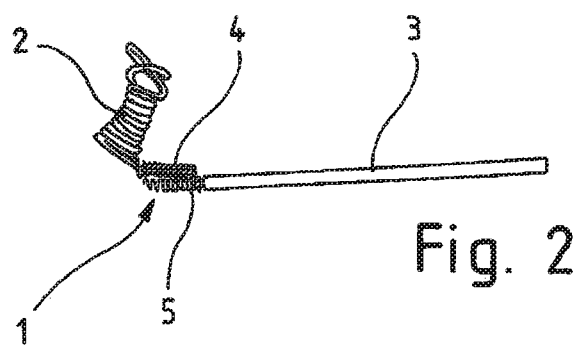
FIG. 2 is the system of FIG. 1 in a second operating state.

In FIG. 2 the system 1 according to the invention of FIG. 1 is shown in the second operating state. In the second operating state the core wire 6 is retracted within the insertion aid 3, whereby the connection between the insertion aid 3 and the medical implant 2 is released. The first helical connecting member 4 of the medical implant 2 is afterwards separated from the second helical connecting member 5 of the insertion aid 3, so that the first helical connecting member 4 and the second helical connecting member 5 no longer engage each other. In the shown second operating state the medical implant 2 is located at the desired implantation site within the human or animal body. After releasing the connection between the medical implant 2 and the insertion aid 3 the insertion aid 3 can be retracted through the catheter (not shown) used during implantation.

Figure 3:
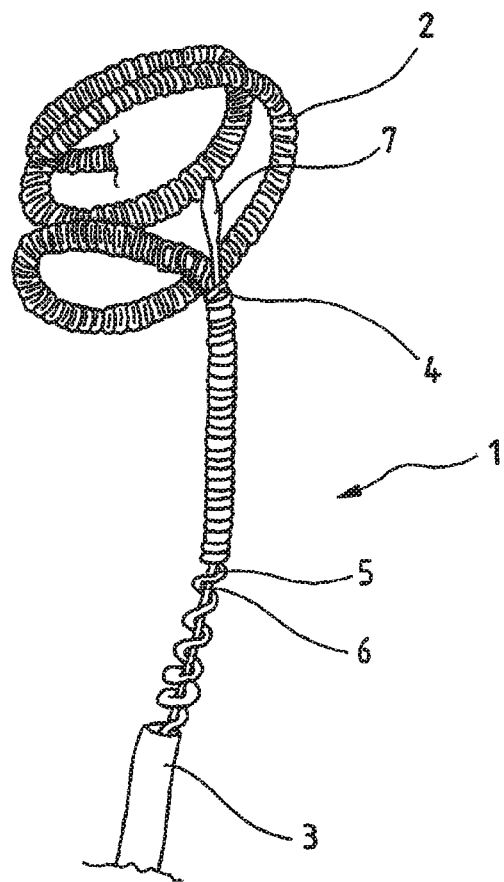
FIG. 3 is a further system according to the invention for connecting a medical implant with an insertion aid in a first operating state.

The system 1 according to the invention for connecting a medical implant 2 with an insertion aid 3 shown in FIG. 3 differs from system 1 of FIG. 1 by the design of the core wire. In the embodiment according to FIG. 3 the core wire 6 has an enlarged cross section 7 at the distal end, which is larger than the inner diameter of the helical ends 4, 5 of the medical implant 2 and the insertion aid 3. Thereby an accidentally release of the medical implant 2 from the insertion aid 3 is prevented. The core wire 6 extends in the shown first operating state in FIG. 3 through the wall of the medical implant 2 outwardly. After exiting the medical implant 2 the core wire 6 is crushed to create the enlarged cross section 7.

LIST OF REFERENCES 1 system
2 implant
3 insertion aid
4 first helical connecting member
5 second helical connecting member
6 core wire
7 enlarged cross section of core wire

What is claimed is:

1. A system for connecting a medical implant to an insertion aid comprising:
  a first helical connecting member at a proximal end of the medical implant, the first helical connecting member having a plurality of turns;
  a second helical connecting member at a distal end of the insertion aid, the second helical connecting member having a plurality of turns;
  a core wire, which in a first operating state of the system, locks the first helical connecting member and the second helical connecting member relative to each other;
  wherein, in the first operating state, the first helical connecting member and the second helical connecting member at least partially engage each other such that at least a portion of the plurality of turns of the first helical connecting member engage with at least a portion of the plurality of turns of the second helical connecting member, and the core wire extends through the engaged turns of the first helical connecting member and the second helical connecting member;
  wherein, in the first operating state, at least one of the first helical connecting member and the second helical connecting member exhibits an elastic restoring force on the core wire; and
  wherein, in a second operating state, in which the core wire is retracted from the engaged turns of the first helical connecting member and the second helical connecting member, the elastic restoring force releases the engaged turns of the first helical connecting member and the second helical connecting member from one another.

2. The system according to claim 1, wherein the first helical connecting member is formed of a first helical connecting member wire and the second helical connecting member is formed of a second helical connecting member wire, and wherein spacing of the plurality of turns of the first helical connecting member from each other corresponds to 1.0 to 2.5 times a diameter of the first helical connecting member wire and/or spacing of the plurality of turns of the second helical connecting member from each other corresponds to 1.0 to 2.5 times a diameter of the second helical connecting member wire.

3. The system according to claim 1, wherein the medical implant, the insertion aid, the first helical connecting member, the second helical connecting member and/or the core wire at least partly comprise a shape-memory material.

4. The system according to claim 3, wherein the shape-memory material comprises a nickel-titanium alloy.

5. The system according to claim 1, wherein the first helical connecting member is formed of a first helical connecting member wire with a diameter between 0.3 mm and 1.5 mm and/or the second helical connecting member is formed of a second helical connecting member wire with a diameter between 0.3 mm to 1.5 mm.

6. The system according to claim 5, wherein the diameter of at least one of the first helical connecting member wire or the second helical connecting member wire is between 0.5 mm and 1.0 mm.

7. The system according to claim 1, wherein the first helical connecting member is arranged angled to the medical implant.

8. The system according to claim 1, wherein the insertion aid is cylindrical and has a hollow space along the longitudinal axis, and wherein the core wire is located within the hollow space and movable relative to the insertion aid along the longitudinal axis of the insertion aid.

9. The system according to claim 1, wherein the core wire has an enlarged cross-section at the distal end.

10. The system according to claim 9, wherein the enlarged cross-section at the distal end is larger than an inner diameter of a helical end of the medical implant and an inner diameter of a helical end of the insertion aid.

\* \* \* \* \*